(12) United States Patent
Barges et al.

(10) Patent No.: US 6,977,086 B1
(45) Date of Patent: Dec. 20, 2005

(54) PHARMACEUTICAL FORMULATION COMPRISING AMOXYCILLIN AND CLAVULANATE

(75) Inventors: Nathalie Claude Marianne Barges, Mayenne (FR); Jacky Andre Gustave Mention, Leognan (FR)

(73) Assignee: Laboratorie GlaxoSmithKline S.A.S., Cedex (FR)

( * ) Notice: Subject to any disclaimer, the term of this patent is extended or adjusted under 35 U.S.C. 154(b) by 229 days.

(21) Appl. No.: 10/069,681

(22) PCT Filed: Aug. 17, 2000

(86) PCT No.: PCT/EP00/08048

§ 371 (c)(1),
(2), (4) Date: Dec. 2, 2002

(87) PCT Pub. No.: WO01/13883

PCT Pub. Date: Mar. 1, 2001

(30) Foreign Application Priority Data

Aug. 20, 1999 (GB) ................................. 9919840
Aug. 25, 1999 (GB) ................................. 9920150
Aug. 3, 2000 (GB) ................................. 0019084

(51) Int. Cl.$^7$ .............................................. A61K 9/14
(52) U.S. Cl. ..................... 424/489; 424/735; 424/765
(58) Field of Search .............................. 424/400, 489, 424/735, 765

(56) References Cited

U.S. PATENT DOCUMENTS 5,114,929 A    5/1992   Vartan ......................... 514/29
5,851,550 A *  12/1998  Martin et al. ............... 424/464

FOREIGN PATENT DOCUMENTS

EP      0 389 177       9/1990
WO      WO 98/35672     8/1998
WO      WO 00/03695     1/2000

* cited by examiner

Primary Examiner—Gary Kunz
Assistant Examiner—Konata M George
(74) Attorney, Agent, or Firm—Dara L. Dinner; Stephen Venetianer; Charles M. Kinzig

(57) ABSTRACT

A pharmaceutical formulation in the form of a dry powder which comprises amoxycillin and clavulanate in a weight ratio of from 2:1 to about 16:1 and a pharmaceutically acceptable carrier or excipient and flavouring agents which provide a straw-berry flavour, further modified by the addition of extra components to add a creamy flavour or an extra fruity flavour.

9 Claims, 2 Drawing Sheets

PHARMACEUTICAL FORMULATION COMPRISING AMOXYCILLIN AND CLAVULANATE

Figure 1:
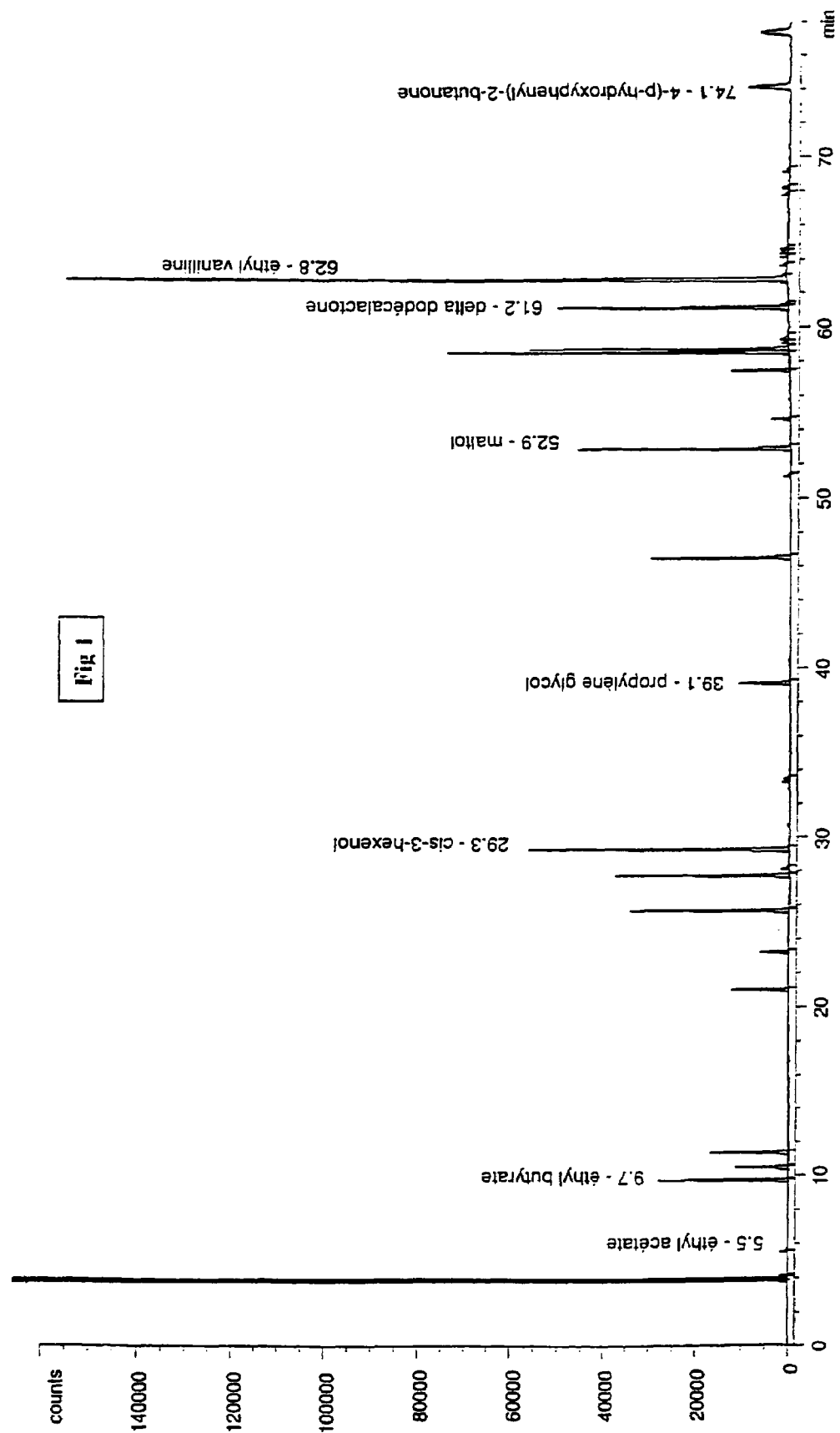

This invention relates to pharmaceutical formulations comprising amoxycillin and a salt of clavulanic acid (hereinafter termed "clavulanate" unless a specific salt is identified) adapted for paediatric administration and which have a particular flavour.

The combination of amoxycillin and clavulanate (co-amoxiclav) is an effective empirical treatment for bacterial infections and may be administered by oral dosing, for instance in the form of tablets, and, for paediatric formulations. as an aqueous solution or suspension, which typically is flavoured. Various co-amoxiclav formulations are marketed by SmithKline Beecham under the trade mark Augmentin.

Paediatric formulations comprising amoxycillin and clavulanate are typically, provided as a dry powder or granules which are reconstituted with water or other aqueous medium prior to first use, generally to form a multiple dose suspension which covers the entire course of therapy. To make then more atractive to a paediatric patient. they typically have a flavour, for instance a fruit flavour, and are also sweetened, for instance with an artifical sweetener. Such formulations have been previously described in inter alia WO 96/34605, WO 97/09042, WO 98/07424 and WO 98/35672 (SmithKline Beecham). Suitable flavours mentioned therein include, for instance orange, banana, raspberry, and golden syrup or mixtures thereof. In WO 98/35672, there is described, as Example 10, a dry powder formulation to be reconstituted as a 100/12.5 mg/ml suspension. This has a strawberry flavour. The recently introduced product Augmentin-Duo 400/57 contains a combination flavour made up of orange dry flavour (61071E), orange dry flavour (9/027108), raspberry dry flavour and golden syrup dry flavour. The flavour of a paediatric formulation is particularly important. especially when the active agents such as amoxycillin have a bitter taste, in encouraging patient compliance. SmithKline Beecham market in the United States under the trade mark "Amoxyl" an amoxycillin powder for oral suspension (125 mg/5 ml) which has a "strawberry" flavour. There is however a continuing need to develop new formulations comprising amoxycillin and clavulanate which have improved flavours.

Accordingly, the present invention provides a pharmaceutical formulation in the form of a dry powder which comprises amoxycillin and clavulanate in a weight ratio of from 2:1 to about 16:1 and a pharmaceutically acceptable carrier or excipient and flavouring agents which provide a strawberry flavour which is modified by the addition of extra components to add a creamy note or an extra fruity note.

The strawberry flavoured product is found to be particularly favoured by potential users. and preferable to existing products having a flavour which is a combination of orange, raspberry and golden syrup flavours. The "creamy" flavour is found to be particularly effective in masking the sulphur taste of amoxycillin.

Strawberry flavours are readily available from commercial sources such as flavour houses, or can be developed by those skilled in the art. It will be appreciated that preferred strawberry flavours will mask the bitter taste of the active ingredients of the formulation not only when the aqueous suspension is freshly prepared but also after standing, for instance after 10 days storage under normal storage conditions. In addition, as the dry powder product ages on shelf storage, the strawberry flavour will need to be effective both at the beginning and end of such storage. Representative strawberry flavours may comprise natural flavours, synthetic equivalents thereof, artificial flavours or mixtures thereof.

Representative additional fruit flavours include peach and passion fruit.

Preferably, a creamy note is added to the basic strawberry flavour. Key components for achieving this include vanillin, maltol (ethyl maltol), δ-dodecalactone, furonol (4-hydroxy-2,5-dimethyl-2,3-dihydrofuran-3-one) and diacetyl.

Preferred strawberry flavours are available from Givaudan-Roure SA (19–23 voie des Bains BP98, 95101. Argenteuil Cedex-France), for instance, the strawberry flavours which have the product codes 11440-31 (Arome Fraise-Passion), 11441-31 (Arome Fraise-Peche), and 11442-31, 11443-31 and 11442-81 (Arome Fraise-Creme). These comprise a mixture of natural flavouring substances, artificial flavouring substances and Nature-identical flavouring substances. Of these, the strawberry flavour with the product code 11442-81 is especially preferred. The major components of these flavours are furonol, maltol, ethyl vanillin, ethyl butyrate, cis-3-hexenol, δ-dodecalactone, furanone, propylene glycol, 4-(p-hydroxyphenyl)-2-butanone, gum arabic, ethyl acetate and diacetyl. It will be appreciated that matching flavours may be produced which may have different components but which are similar or equivalent under organoleptic evaluation and/or sensory analysis. The present invention includes all such matching flavours.

Preferably, the flavour is provided as a dry powder with the flavour encapsulated in a suitable base to allow it to retain its desirable organoleptic properties for the shelf life of the active product. Typical examples are "trusil", "permaseal", "ultraseal", and "durarome". In a representative example, the flavour is provided as a "permaseal" flavour, that is atomised with a porous structure and particle size in the range 100 to 150 μm.

Preferably, the modified strawberry flavour is incorporated into the dry formulation as a dry flavour. Preferably, the flavour is present in form 0.5 to 5%, more preferably 1 to 4%, by weight of the dry powder formulation.

Dry powder formulations may be provided as a unit dosage in a sachet, for addition to water immediately prior to use, or, for oral administration to paediatric patients, adapted for reconstitution into a multiple dose aqueous suspension.

In the formulations of the invention, amoxycillin may be in the form of sodium amoxycillin, or, preferably, amoxycillin trihydrate. Clavulanate is preferably in the form of potassium clavulanate. Potassium clavulanate is extremely moisture-sensitive and should be stored and handled in conditions of 30% RH or less, ideally as low as possible. Formulations should be packaged in atmospheric moisture-proof containers, and such formulations and/or their containers may contain a desiccant.

Preferably, formulations of the present invention comprise amoxycillin and clavulanate in a weight ratio which is 4:1, 7:1, 8:1, or 14:1. Preferably the paediatric formulations will provide on reconstitution about 125/31.25, 250/62.5, 200/28.5, 250/31.25, 400/57, 500/62.5, 500/125 or 600/42.9 mg amox/clav per 5 ml of suspension. Representative sachets include 400/57 mg amox/clav.

The weight ratios of amoxycillin:clavulanate expressed herein are as free acid equivalent.

The dry powder formulations of the present invention may optionally comprise granules, for instance granules of amoxycillin and/or amoxycillin and potassium clavulanate, as described in WO 98/35672 (Smith Kline Beecham).

Generally the proportion of active materials amoxycillin trihydrate and potassium clavulanate in a formulation of the invention, before reconstitution, may be around 60 to 80% by weight of the initial formulation.

The formulations of this invention will normally include, in addition to its active materials amoxycillin trihydrate and potassium clavulanate, excipients which are standard in the field of formulations adapted for reconstitution into aqueous suspensions for oral dosing to paediatric patients. Such excipients will be used in generally standard proportions, and at generally standard particle sizes and grades etc.

Such excipients may comprise suspension aids, glidants (to aid filling), diluents, bulking agents, sweetening agents, stabilisers, pH modifiers, preservatives, etc. In addition, the formulations may also comprise an edible desiccant to assist preservation of the potassium clavulanate against hydrolysis by atmospheric moisture on storage. Potassium clavulanate is normally supplied in admixture with silicon dioxide as diluent, typically as a 1:1 blend.

Preferred excipients include xanthan gum (suspension aid), colloidal silicon dioxide (glidant), hydroxypropylmethylcellulose (suspension aid), sodium benzoate (preservative), magnesium stearate and silicon dioxide (silica gel, desiccant, diluent for potassium clavulanate and bulking agent) and succinic acid (pH modifier). Preferred sweetening agents include artificial sweetners such as aspartame.

Preferably, excipients are present in from 20 to 40% by weight of the initial formulation.

In a preferred embodiment, a dry powder formulation comprises granules of amoxycillin and clavulanate in a 2:1 ratio and granules of amoxycillin, preferably to give an overall ratio of 7:1 or 8:1, as described in WO 98/35672. The preferred granules of amoxycillin and clavulanate described therein further comprise silica gel present in from 5 to 15 wt % of potassium clavulanate, typically about 10 wt %; and CLPVP present in from 0.5 to 5 wt % of amoxycillin trihydrate, preferably 1 to 4 wt %, typically about 3%. The relatively lower level of silica gel allows a reduction in the amount of flavour that is needed, to between 2 and 5%, preferably 2.5 to 3.5%, typically about 3%. Preferred extragranular excipients include silica gel (to give an overall total of from 5 to 15, preferably 8 to 12% by weight of the formulation), carboxymethylcellulose sodium salt (present in from 3 to 6% by weight of the formulation), xanthan gum (present in from 0.2 to 1% by weight of the formulation), sodium benzoate, colloidal silica and magnesium stearate and a sweetening agent, preferably aspartame. Preferably such granules are prepared by roller compaction, followed by milling and sieving, to achieve a preferred size fraction. Granules are preferably in the size range $1\mu$ to 300 $\mu$m, especially 10 $\mu$m to 200 $\mu$m. A tyical size 70% or more.

Formulations of the present invention may be manufactured using techniques which are generally conventional in the manufacture of dry formulations for reconstitution into aqueous suspensions. For example, a suitable technique is that of mixing dry powdered or granulated ingredients for loading into a suitable container.

Formulations of the present invention are preferably provided in an atmospheric moisture-proof container or a sachet for reconstitution with water or other suitable aqueous medium shortly prior to use. Preferably, a dry powder formulation is provided in a bottle with a moisture-proof cap.

For convenience of dosing, the amount of powder provided in a bottle and the volume of water used to reconstitute the powder are determined so that a unit dosage is provided in a convenient volume, for instance from 2.5 to 10 $\mu$ml, typically about 5 ml of reconstituted suspension. Typically, the bottle will comprise the whole course of therapy, so that reconstituted suspension will be a multiple dose suspension.

It will be appreciated that a preferred unit dosage quantity will be one which enables the administration of the above-mentioned daily dosage quantity, divided between two bid doses, e.g. half of the above-mentioned daily dose, in a volume of a suspension which acceptable for oral administration to a paediatric patient, preferably between 2.5 to 10 $\mu$ml, typically about 5 ml. Such administration may be by a spoon, for instance a calibrated spoon or a graduated, a blunt-ended syringe or a calibrated dosing pump.

Representative formulations are described in WO 96/34605, WO 97/09042, WO 98/07424 and WO 98/35672 (SmithKline Beecham).

The invention will now be described by way of example.

EXAMPLE 1

Formulation to Give 100 mg/12.5 mg/ml Suspension (8:1 ratio)

A. Granules of amoxycillin trihydrate and granules of amoxycillin trihydrate and potassium clavulanate (ratio 2:1) were prepared using the procedures described in Examples 1 and 5 of WO 98/35672 (SmithKline Beecham).

The granules were then blended in the appropriate ratio with typical suspension excipients to produce a formulation comprising:

| | |
|---|---:|
| Amoxycillin trihydrate 100% of theory (equivalent to 3000 mg Amoxycillin 100%) | 3443.22 mg |
| Potassium Clavulanate 100% of theory (equivalent to 375 mg Clavulanic acid 100%) | 446.79 |
| CLPVP (intra-granular) | 103.29 |
| Silica gel[1] (intra-granular) | 44.68 |
| Silica gel[1] (extra-granular) | 500.00 |
| Xanthan gum | 25.20 |
| Carboxymethylcellulose sodium salt | 250.00 |
| Sodium benzoate | 51.00 |
| Hydrophobic colloidal silica | 15.00 |
| Aspartame | 96.00 |
| Magnesium stearate | 10.00 |
| Creamy strawberry flavour[2] | 150.00 |
| Total weight | 5135.50 mg |

[1]Syloid AL-1
[2]creamy strawberry flavour (arome fraise crème) 1142-81 (Givaudan-Roure)

The formulation is provided in a glass bottle and made up into 30 ml of aqueous solution immediately prior to first use, to give a notional quantity of 100/12.5 mg per ml of reconstituted aqueous solution. An appropriate dosage, to provide a dosage of 80 mg/kg/day, taken in three dosages, is measured using a 4 ml graduated pipette.

B. A further formulation may be provided using twice the quantities given above in A. This formulation is provided in a glass bottle and made up into 60 ml of aqueous solution immediately prior to first use, to give a notional quantity of 100/12.5 mg per ml of reconstituted aqueous solution. An appropriate dosage, to provide a dosage of 80 mg/kg/day, taken in three dosages, is measured using a 5 ml measuring spoon or a 8 ml graduated pipette.

EXAMPLE 2

Formulation to Give 400/57 mg/5 ml Suspension

Granules of amoxycillin trihydrate and granules of amoxycillin trihydrate and potassium clavulanate (ratio 2:1) were prepared using the procedures described in Examples 1 and 5 of WO 98/35672 (SmithKline Beecham).

The granulates were then blended in the appropriate ratio with typical suspension excipients to produce a formulation comprising expressed in mg/5 ml as unit formula:

| | |
|---|---:|
| Amoxycillin trihydrate 100% of theory (equivalent to 400 mg Amoxycillin 100%) | 472.81 mg |
| Potassium Clavulanate 100% of theory (equivalent to 60 mg Clavulanic acid 100%) | 71.51 mg |
| CLPVP (intra-granular) | 14.18 |
| Silica gel[1] (intra-granular) | 7.151 |
| Silica gel[1] (extra-granular) | 86.66 |
| Xanthan gum | 4.42 |
| Carboxymethylcellulose sodium salt | 43.42 |
| Sodium benzoate | 51.00 |
| Hydrophobic colloidal silica | 2.60 |
| Aspartame | 16.64 |
| Magnesium stearate | 1.73 |
| Creamy strawberry flavour[2] | 26.00 |
| Total weight (5 ml) | 798.121 mg |

[1] Syloid AL-1
[2] creamy strawberry flavour (arome frais crème) 1142-81 (Givaudan-Roure)

The formulation is provided in a suitable glass bottle and made up into either 30, 70 or 140 ml of aqueous solution immediately prior to first use, to give a notional quantity of 400/57 mg per 5 ml of reconstituted aqueous solution.

Analysis of Strawberry Flavour ref 1142-81

Strawberry flavour ref 1142-81 was analysed by capillary gas phase chromatography. A sample thereof (3 g) was partitioned between water and ether/pentane(70:30), the organic layer being then dreid and concentrated under reduced pressure in a rotary evaporator at 30 to 35° C. The conditions for the analysis were as follows:

| | |
|---|---|
| Column: | Carbowax 20M, 25 m*0.32 mm |
| Oven: | gradient - initial temperature 40° C. for 10 min, then 3° C./min from 40 to 160° C., followed by 10° C./min from 160 to 240° C. and finally 240° C. for 20 min |
| Detector: | FID/250° C. |
| Inj Volume: | 5 µl |
| Injector: | split, at 200° C. |
| Gas: | N$_2$ at 100 ml/min |
| Instrument: | HP 5890 series II |

The resultant chromatogram is shown as FIG. 1.

The strawberry flavour was also analysed by an alternative method involving analysis of the "headspace" by capillary gas phase chromatography, using a flame ionisation detector (Perkin Elmer E 8700).

| | |
|---|---|
| Column: | Carbowax 20M, 50 m × 0.22 mm |
| Gas: | Nitrogen at 30 PSI (env. 1.7 ml) |
| Injector temperature | 170° C. |
| Detector: | FID at 270° C. (air flow 300 ml/min, hydrogen flow 30 ml/min, auxiliary gas flow 30 ml/mn |
| Headspace heater | temperature 140° C. |
| Gradient: | 40° C. for 10 min, 4° C./min for 40° C. to 150° C., 10° C./min for 150° C. to 220° C., 220° C. for 3 min |

A sample of the strawberry flavour powder was introduced into a special bottle for headspace injection and maintained for 40 min at temperature before injection.

Figure 2:
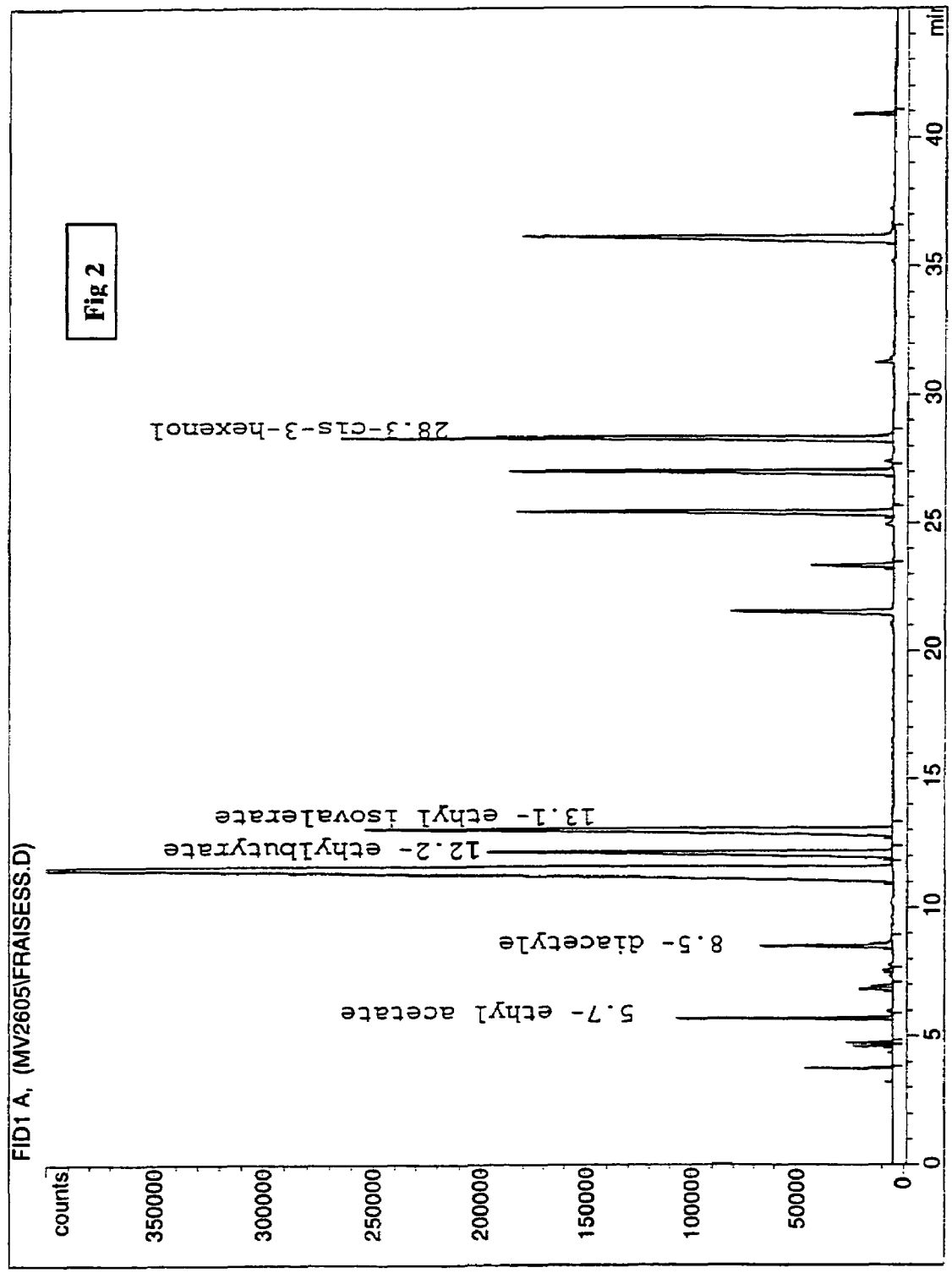

This gave peaks for ethyl acetate, diacetyl, ethyl butyrate, ethyl isovalerate and cis-3-hexenol, as shown in FIG. 2.

What is claimed is:

1. A pharmaceutical formulation in the form of a dry powder which comprises amoxycillin and clavulanate in a weight ratio of from 2:1 to about 16:1 and a pharmaceutically acceptable carrier or excipient and flavourinq agents which provide a strawberry flavour which is modified by the addition of extra components to add a creamy flavour or an extra fruity flavour, wherein the creamy flavour is provided by a blend of vanillin, maltol (ethyl maltol), δ-dodecalactone, furonol (4-hydroxy-2,5-dimethyl-2,3-dihydrofuran-3-one) and diacetyl.

2. A pharmaceutical formulation in the form of a dry powder which comprises amoxycillin and clavulanate in a weight ratio of from 2:1 to about 16:1 and a pharmaceutically acceptable carrier or excipient and flavouring agents which provide a strawberry flavour which is modified by the addition of extra components to add a creamy flavour or an extra fruity flavour, wherein the major components of the flavouring agents are furonol, maltol, ethyl vanillin, ethyl butyrate, cis-3-hexenol, δ-dodecalactone, furanone, propylene glycol, 4-(p-hydroxyphenyl)-2-butanone, gum arabic, ethyl acetate and diacetyl.

3. A formulation as claimed in claim 2 which has a matching flavour.

4. A pharmaceutical formulation in the form of a dry powder which comprises amoxicillin granules, and clavulanate in a weight ratio of from 2:1 to about 16:1 and a pharmaceutically acceptable carrier or excipient and flavouring agents which provides a strawberry flavour which is modified by the addition of extra components to add a creamy flavour or an extra fruity flavour, and which further comprises as an extra-granular excipient silica gel (to give an overall total of from about 5 to 15% by weight of the formulation), carboxymethylcellulose sodium salt (present in from about 3 to 6% by weight of the formulation), xanthan gum (present in from about 0.2 to 1% by weight of the formulation), sodium benzoate, colloidal silica and magnesium stearate and a sweetening agent.

5. A pharmaceutical formulation in the form of a dry powder, which comprises an 8:1 weight ratio of amoxycillin and clavulanate, comprising:

| | |
|---|---:|
| Amoxycillin trihydrate 100% of theory (equivalent to 3000 mg Amoxycillin 100%) | 3443.22 mg |
| Potassium Clavulanate 100% of theory (equivalent to 375 mg clavulanate acid 100%) | 446.79 |
| CLPVP (intra-granular) | 103.29 |
| Silica gel (intra-granular) | 44.68 |
| Silica gel (extra-granular) | 500.00 |
| Xanthan gum | 25.20 |
| Carboxymethylcellulose sodium salt | 250.00 |
| Sodium benzoate | 51.00 |

-continued

| | |
|---|---|
| Hydrophobic colloidal silica | 15.00 |
| Aspartame | 96.00 |
| Magnesium stearate | 10.00 |
| Creamy strawberry flavour | 150.00 |
| Total weight | 5135.50 mg. |

6. A pharmaceutical formulation in the form of a dry powder, which comprises a 7:1 weight ratio of amoxycillin and clavulanate, comprising:

| | |
|---|---|
| Amoxycillin trihydrate 100% of theory (equivalent to 400 mg Amoxycillin 100%) | 472.81 mg |
| Potassium Clavulanate 100% of theory (equivalent to 60 mg clavulanate acid 100%) | 71.51 |
| CLPVP (intra-granular) | 14.18 |
| Silica gel (intra-granular) | 7.151 |
| Silica gel (extra-granular) | 86.66 |
| Xanthan gum | 4.42 |
| Carboxymethylcellulose sodium salt | 43.42 |
| Sodium benzoate | 51.00 |
| Hydrophobic colloidal silica | 2.6 |
| Aspartame | 16.64 |

-continued

| | |
|---|---|
| Magnesium stearate | 1.73 |
| Creamy strawberry flavour | 26.00 |
| Total weight (5 ml) | 798.121 mg. |

7. A formulation as claimed in claim 4 wherein the silica gel is present from about 8 to 12% by weight.

8. A formulation as claimed in claim 4 wherein the sweetening agent is aspartame.

9. A pharmaceutical formulation in the form of a dry powder which comprises granules of amoxicillin, and granules of clavulanate in a weight ratio of from 2:1 to about 16:1 and a pharmaceutically acceptable carrier or excipient and flavouring agents which provides a strawberry flavour which is modified by the addition of extra components to add a creamy flavour or an extra fruity flavour, and which further comprises as an extra-granular excipient silica gel (to give an overall total of from about 5 to 15% by weight of the formulation), carboxymethylcellulose sodium salt (present in from about 3 to 6% by weight of the formulation), xanthan gum (present in from about 0.2 to 1% by weight of the formulation), sodium benzoate, colloidal silica and magnesium stearate and a sweetening agent.

\* \* \* \* \*